United States Patent [19]

Sorokin

[11] Patent Number: 5,741,755
[45] Date of Patent: Apr. 21, 1998

[54] HERBICIDAL COMPOSITION AND A METHOD TO CONTROL UNDESIRED VEGETATION

[75] Inventor: Vladimir Iosifovich Sorokin, Moscow, Russian Federation

[73] Assignee: Kare Ltd., Riga, Latvia

[21] Appl. No.: 392,869

[22] PCT Filed: Sep. 2, 1993

[86] PCT No.: PCT/RU93/00211

§ 371 Date: Jun. 22, 1995

§ 102(e) Date: Jun. 22, 1995

[87] PCT Pub. No.: WO95/05155

PCT Pub. Date: Mar. 17, 1994

[30] Foreign Application Priority Data

Sep. 4, 1992 [SU] U.S.S.R. .................................. 5061695

[51] Int. Cl.⁶ .............................. A01N 43/64; A01N 47/10
[52] U.S. Cl. ........................ 504/135; 504/168; 504/171
[58] Field of Search ........................... 504/135, 168, 504/171

*Primary Examiner*—Allen J. Robinson
*Attorney, Agent, or Firm*—Cammarata & Grandinetti

[57] ABSTRACT

This invention is related to herbicidal compositions comprising derivatives of benzenesulfonylurea and 2-methoxy-3,6-dichlorobenzoic acid for control of undesired vegetation by treating said vegetation and locus to be protected by said compositions.

To eliminate the detrimental effects on crop rotation by lowering dosage of herbicide and to widen its activity spectrum a herbicidal composition is proposed comprising a mixture of ammonium salts of benzenesulfonylurea derivatives and of 2-methoxy-3,6-dichlorobenzoic acid with additives.

The treatment of the vegetation and locus is performed by water solution of the disclosed composition with the dosage in the range of 50–500 g/ha of composition.

5 Claims, No Drawings

HERBICIDAL COMPOSITION AND A METHOD TO CONTROL UNDESIRED VEGETATION

This application is a 371 of PCT/RU93/00211, filed Sep. 2, 1993.

FIELD OF UTILITY

The instant application is related to agriculture, specifically to chemical agents for plant protection and eradication of undesired vegetation.

BACKGROUND OF THE INVENTION

Derivatives of sulfonylurea of general formula

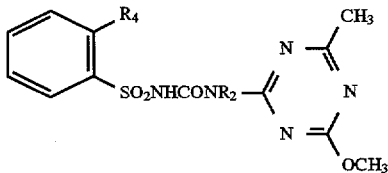

wherein $R_1$=Cl, COOCH$_3$, OCH$_2$CH$_2$Cl and $R_2$=H, CH$_3$ are known as herbicides for control of weeds in cereals [1].

All herbicides of the sulfonylurea series have considerable advantage compared to other herbicides because of the low dosage (8–50 g/ha of active principle) and high selectivity, although their low degradation rate in soil causes detrimental effects in crop rotation as well as resistance in a number of weeds. Accidental over-dosage of these herbicides can result in serious phytotoxicity for certain cereals.

All known herbicidal compositions based on sulfonylurea are wettable powders or microgranules. The absence of water-soluble preparations in these series is explainable by low water-solubility of sulfonylurea and their relatively high hydrolysis rate.

The use of 2-methoxy-3,6-dichlorobenzoic acid and its salts as herbicides to control weeds in cereals by application of 150 g/ha of the active principle is known (preparation Banvel-D or Dicamba) [2] The advantage of this herbicide is the complete absence of resistance to it in weeds. Nevertheless the relatively high dosage of the preparation and rather narrow spectrum of activity is a disadvantage.

Increasing of the herbicidal activity of 2-methoxy-3,6-dichlorobenzoic acid and lowering its dosage as well as elimination of disadvantages inherent to known herbicides of benzenesulfonylurea series poses a problem of creation of herbicidal composition with low dosage and wide activity spectrum, absence of detrimental effects on crop rotation and phytotoxicity in crops to be protected, and not leading to development of resistance in weeds.

The most advantageous solution of this problem is a composition for control of undesired vegetation comprising a mixture based on benzenesulfonylurea derivative

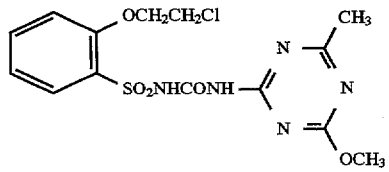

and 2-methoxy-3,6-dichlorobenzoic acid with the addition of surfactant, organic solvent and water [3].

A method for control of undesired vegetation in cereals is known. It comprises the application of emulsion or suspension of the aforementioned herbicidal composition on basis of benzenesulfonylurea derivative and 2-methoxy-3,6-dichlorobenzoic acid with addition of a surfactant, organic solvent and water. The application dosage to weeds is 3 kg/ha. No exact examples describing the components of the composition and method of its application are disclosed.

DETAILED DESCRIPTION OF THE INVENTION

The instant invention discloses a herbicidal composition for use in cereals, comprising ammonium salts of benzenesulfonylureas of general formula (I)

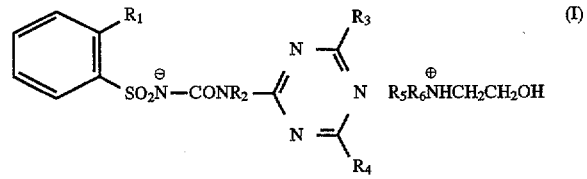

wherein:

$R_1$=Cl, COOCH$_3$ or OCH$_2$CH$_2$Cl;

$R_2$=H or CH$_3$;

$R_3$=CH$_3$ or N(CH$_3$)$_2$;

$R_4$=OCH$_3$ or ON=C(CH$_3$)$_2$;

$R_5$=CH$_3$ or C$_2$H$_5$;

$R_6$=C$_2$H$_5$ or CH$_2$CH$_2$OH, together with ammonium salt of 2-methoxy-3,6-dichlorobenzoic acid of general formula (II)

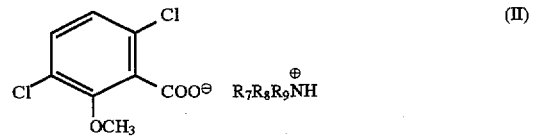

wherein:

$R_7$=CH$_3$ or C$_2$H$_5$;

$R_8$=H, CH$_3$ or CH$_2$CH$_2$OH;

$R_9$=H, C$_2$H$_5$ or CH$_2$CH$_2$OH a surfactant, an organic solvent and water with the following weight percentage of components:

| | |
|---|---|
| ammonium salt of benzenesulfonylurea derivative | 2,0–50 |
| ammonium salt of 2-methoxy-3,6-dichlorobenzoic acid | 5,0–50 |
| surfactant | 1,0–5,0 |
| organic solvent | 10–40 |
| water | up to 100. |

As surfactants the following agents are applicable: bis-polyoxyethylated alkylamine, sodium bis(2-ethylhexyl) succinate sulfonate, polyethyleneglycol monoalkyl ethers or alkylaryl ethers of polyethyleneglycol or polypropyleneglycol.

Triethyleneglycol is used as organic solvent. A method for control of undesired vegetation in cereals comprises applying to the locus to be protected a herbicidal composition based on derivative of benzenesulfonylurea, 2-methoxy-3,6-dichlorobenzoic acid with addition of surfactant, organic solvent and water is characterized in that benzenesulfonylurea derivative and 2-methoxy-3,6-dichlorobenzoic acid are employed in the form of their ammonium salts with the respective general formulas (I) and (II)

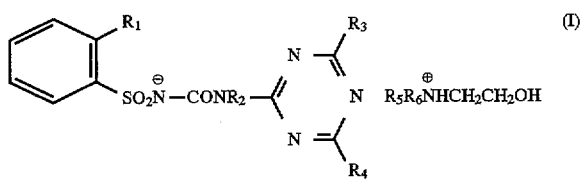

wherein:
$R_1$=Cl, CCOCH$_3$ or OCH$_2$CH$_2$Cl;
$R_2$=H or CH$_3$;
$R_3$=CH$_3$ or N(CH$_3$)$_2$;
$R_4$=OCH$_3$ or ON=C(CH$_3$)$_2$;
$R_5$=CH$_3$ or C$_2$H$_5$;
$R_6$=C$_2$H$_5$ or CH$_2$CH$_2$OH, and

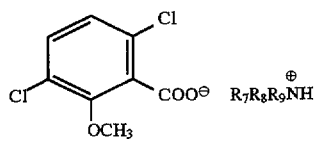

wherein:
$R_7$=CH$_3$ or C$_2$H$_5$;
$R_8$=H, CH$_3$ or CH$_2$CH$_2$OH;
$R_9$=H, C$_2$H$_5$ or CH$_2$CH$_2$OH
with the following weight percentage of components:

| | |
|---|---|
| ammonium salt of benzenesulfonylurea derivative | 2,0–50 |
| ammonium salt of 2-methoxy-3,6-dichlorobenzoic acid | 5,0–50 |
| surfactant | 1,0–5,0 |
| organic solvent | 10–40 |
| water | up to 100. |

The dosage of active principles is 25–125 g/ha.

The invention is further illustrated by the following examples.

EXAMPLE 1

Diethylethanolammonium salt of 1-(2-chlorobenzenesulfonyl)-3-(4-methyl-6-methoxy-1,3,5-triazin-2-yl)urea The reaction vessel was charged with 357 g (1 Mole) of 1-(2-chlorobenzene sulfonyl)-3-(4-methyl-6-methoxy-1,3,5-triazin-2-yl)urea, 117 g (1 Mole) or diethylaminoethanol and 10 L of water and the suspension was stirred at room temperature until solution was complete. The solvent was evaporated on rotary vacuum evaporator and the product collected in quantitative yield.

Elemental analyses and physico-chemical data for the ammonium salts of the sulfonylureas, prepared by the method described in Example 1 are presented in Table 1.

EXAMPLE 2

Diethylethanolammonium salt of 2-methoxy-3,6-dichlorobenzoic acid

The reaction vessel was charged with 221 g (1 Mole) of 2-methoxy-3,6-dichlorobenzoic acid, 117 g (1 Mole) of diethylaminoethanol and 2 L of water and the suspension stirred at 50° C. until solution was complete. The solvent was evaporated on rotary vacuum evaporator and the product collected in quantitative yield.

By the method described in Example 2 dimethylammonium and ethyldiethanolammonium salts were prepared. Elemental analyses for the salts are presented in Table 2.

EXAMPLE 3

Herbicidal Composition

The reaction vessel was charged with calculated amounts of the ammonium salt of benzenesulfonylurea (I) and calculated amounts of the ammonium salt of 2-methoxy-3,6-dichlorobenzoic acid (II), the quantity of the latter depending on the chosen ratio of the two components (mass ratio from 10:1 to 1:25). The necessary quantity of surfactant, triethyleneglycol and water was added and the mixture was stirred at room temperature till the solution was completed.

Examples of herbicidal compositions with different ratios of constituents are presented in Table 3.

EXAMPLE 4

Laboratory Testing of Herbicidal Compositions (Examples 1.1, 1.2 and 1.3)

Herbicidal compositions with different ratios of ammonium salts of benzenesulfonylureas (I) and 2-methoxy-3,6-dichlorobenzoic acid (II) were tested in greenhouse. In vegetation experiments for crops and weeds the following species were used: wheat, corn, lambsquarters, corn grass, ryegrass, sortell, pigweed and corn poppy. The treatment of growing plants was performed for cereals at the third leaf phase, for other species—at the appearance of the second true leaf phase. The dosage of the herbicidal composition was 100 g/ha. The humidity of soil was kept at 60–70% of saturation by daily watering. The effectiveness of herbicidal compositions was evaluated on the 14th day after spray application. The results obtained show a considerable synergism of combined application of herbicides (I) and (II). The results are presented in Tables 4–7.

EXAMPLE 5

Field Tests on Wheat

Area under spring wheat (Moskovskaya 35) was weeded mainly with lambsquarters, hemp nettle, scentless chamomile, catchweed bedstraw, sow thistle and chickweed. The herbicidal compositions were applied at the bushing stage of crop in dosage 500 L/ha of their water solution.

The field tests confirmed the substantial synergism of components in the herbicidal composition.

Results presented in Tables 8–9 show that application of the mixture of herbicides effectively protects crops like wheat at substantially lower dosage thus making the mixed preparation safe for crop rotation. The use of herbicidal compositions of the instant invention permits the lowering the dosage of salt of benzenesulfonylurea derivative (I) from 2 to 5 times and dosage of 2-methoxy-3,6-dichlorobenzoic acid salt (II)—3 times in comparison with the application of individual chemicals and increases their effectiveness.

EXAMPLE 6

Field Tests on Corn

Tests were performed on area under corn (hybrid POCC-144). Herbicidal compositions were applied as water solutions at 3–5 leaf phase of corn. The main weeds were millet species—48–77% and dicotyledonous—33–52%. The percentage of barnyard grass in millet species was 32–59%. 85–96% of the dicotyledonous consisted of pigweed. The results presented in Table 7 show that the herbicidal composition of the instant invention effectively controls dicotyledonous weeds and effects a considerable phytotoxicity towards monocotyledonous weeds. The application of mixed herbicidal comsitions based on derivative of benzenesulfonylurea (IB) and 2-methoxy-3,6-dichlorobenzoic acid (II) results in lowering dosage of (IB) 1.5 times and (II) 2–8 times, substantially increasing the effectiveness of preparations for weed control.

The herbicidal compositions of the instant invention displayed special effectiveness in control of undesired vegetation in areas under grain cereals and corn.

Related Information

[1] C. Smith, Sulfonylurea herbicides, 1991, PJB Publication Ltd., p. 51, 67, 99, 107

[2] N. N. Mel'nikov, K. V. Novozhilov, T. M. Ryzhkova, Khimicheskie sredstva zashchity rastenil', 1980, "Khimiya", Moscow, p. 27

[3] EP application #9236273

TABLE 1

| HERBICIDAL COMPOSITION | Percentage of components [weight %] | | | | |
|---|---|---|---|---|---|
| Variants | a | b | c | d | e |
| 1 | 2 | 3 | 4 | 5 | 6 |
| 1.1 Diethylethanolammonium salt (IA) $R_1 = Cl$; $R_2 = H$, $R_3 = CH_3$, $R_4 = OCH_3$ | 2 | 4 | 2 | 10 | 10 |
| Dimethylammonium sait (II) | 50 | 40 | 40 | 10 | 50 |
| Surfactant | 1 | 2 | 3 | 2 | 5 |
| Triethyleneglycol | 17 | 20 | 20 | 35 | 10 |
| Water | 30 | 34 | 35 | 43 | 25 |
| 1.2 Diethylethanolammonium salt (IB) $R_1 = Cl$, $R_2 = H$, $R_3 = N(CH_3)_2$, $R_4 = -ON=C(CH_3)_2$ | 2.5 | 25 | 25 | 25 | 50 |
| Dimethylammonium salt (II) | 5 | 10 | 15 | 25 | 25 |
| Surfactant | 2.5 | 2 | 2 | 2 | 4 |
| Triethyleneglycol | 30 | 23 | 23 | 13 | 11 |
| Water | 60 | 40 | 35 | 35 | 10 |
| 1.3 Diethylethanolammonium salt (IA) $R_1 = Cl$, $R_2 = H$, $R_3 = CH_3$, $R_4 = OCH_3$ | 1 | 1 | 3 | 7 | 7 |
| Diethylethanolammonium salt (IB) $R_1 = Cl$, $R_2 = H$, $R_3 = N(CH_3)_2$, $R_4 = -ON=C(CH_3)_2$ | 2 | 2 | 6 | 14 | 14 |
| Dimethylammonium salt (II) | 10 | 50 | 30 | 10 | 50 |
| Diethylaminoethanol | 5 | 3 | 4 | 5 | 2 |
| Triethyleneglycol | 32 | 14 | 17 | 24 | 7 |
| Water | 50 | 30 | 40 | 40 | 20 |
| 1.4 Ethyldiethanolammonium salt (IC) $R_1 = COOCH_3$, $R_2 = H$, $R_3 = CH_3$, $R_4 = OCH_3$ | 2 | 2 | | | |
| Ethyldiethanolammonium salt (II) | 40 | 40 | | | |
| Surfactant | 3 | 2 | | | |
| Triethyleneglycol | 15 | 31 | | | |
| Water | 40 | 25 | | | |
| 1.5 Ethyldiethanolammonium salt (ID) $R_1 = OCH_2CH_2Cl$, $R_2 = H$, $R_3 = CH_3$, $R_4 = OCH_3$ | 2 | 4 | | | |
| Ethyldiethanolammonium salt (II) | 40 | 40 | | | |
| Surfactant | 3 | 2 | | | |
| Triethyleneglycol | 15 | 14 | | | |
| Water | 40 | 40 | | | |
| 1.6 Ethyldiethanolammonium salt (IC) $R_1 = COOCH_3$, $R_2 = H$, $R_3 = CH_3$, $R_4 = OCH_3$ | 2 | 8 | | | |
| Ethyldiethanolammonium salt (II) | 40 | 40 | | | |
| Surfactant | 3 | 2 | | | |
| Triethyleneglycol | 25 | 25 | | | |
| Water | 30 | 25 | | | |
| 1.7 Diethylethanolammonium salt (IA) $R_1 = Cl$, $R_2 = H$, $R_3 = CH_3$, $R_4 = OCH_3$ | | 2 | 3 | 5 | 8 |
| Diethylethanolammonium salt (II) | | 50 | 45 | 50 | 48 |
| Tenside | | 3 | 2 | 2 | 2 |
| Triethyleneglycol | | 20 | 25 | 25 | 20 |
| Water | | 25 | 25 | 18 | 22 |
| 1.8 Diethylethanolammonium salt (IG) $R_1 = Cl$, $R_2 = CH_3$, $R_3 = CH_3$, $R_4 = OCH_3$ | 2 | 4 | 6 | 8 | 10 |
| Diethylethanolammonium salt (II) | 50 | 40 | 42 | 48 | 50 |
| Tenside | 2 | 2 | 2 | 3 | 3 |
| Triethyleneglycol | 20 | 24 | 25 | 21 | 17 |
| Water | 26 | 30 | 25 | 20 | 20 |
| 1.9 Diethylethanolammonium salt (IF) $R_1 = COOCH_3$, $R_2 = CH_3$, $R_3 = CH_3$, $R_4 = OCH_3$ | 4 | 10 | | | |
| Diethylethanolammonium salt (II) | 40 | 50 | | | |
| Tenside | 3 | 2 | | | |
| Triethyleneglycol | 25 | 18 | | | |
| Water | 28 | 20 | | | |

TABLE 2

| # | $R_1$ | $R_2$ | $R_3$ | $R_4$ | $R_5$ | $R_6$ | Summary formula |
|---|---|---|---|---|---|---|---|
| 1. | Cl | H | $CH_3$ | $OCH_3$ | $CH_3$ | $CH_3$ | $C_{16}H_{23}ClN_6O_5S$ |
| 2. | Cl | H | $CH_3$ | $OCH_3$ | $C_2H_5$ | $C_2H_5$ | $C_{18}H_{27}ClN_6O_5S$ |
| 3. | Cl | H | $CH_3$ | $OCH_3$ | $C_2H_5$ | $CH_2CH_2OH$ | $C_{18}H_{27}ClN_6O_6S$ |
| 4. | Cl | CH | $CH_3$ | $OCH_3$ | $C_2H_5$ | $C_2H_5$ | $C_{19}H_{29}ClN_6O_5S$ |
| 5. | Cl | $CH_3$ | $CH_3$ | $OCH_3$ | $C_2H_5$ | $CH_2CH_2OH$ | $C_{19}H_{29}ClN_6O_6S$ |
| 6. | Cl | H | $N(CH_3)_2$ | $ONC(CH_3)_2$ | $C_2H_5$ | $C_2H_5$ | $C_{21}H_{33}ClN_8O_5S$ |
| 7. | $COOCH_3$ | H | $CH_3$ | $OCH_3$ | $CH_3$ | $CH_3$ | $C_{18}H_{26}N_6O_7S$ |
| 8. | $COOCH_3$ | H | $CH_3$ | $OCH_3$ | $C_2H_5$ | $C_2H_5$ | $C_{20}H_{30}N_6O_7S$ |
| 9. | $COOCH_3$ | H | $CH_3$ | $OCH_3$ | $C_2H_5$ | $CH_2CH_2OH$ | $C_{20}H_{30}N_6O_8S$ |
| 10. | $COOCH_3$ | $CH_3$ | $CH_3$ | $OCH_3$ | $C_2H_5$ | $C_2H_5$ | $C_{21}H_{32}N_6O_7S$ |
| 11. | $COOCH_3$ | $CH_3$ | $CH_3$ | $OCH_3$ | $C_2H_5$ | $CH_2CH_2OH$ | $C_{21}H_{32}N_6O_8S$ |
| 12. | $OCH_2CH_2Cl$ | H | $CH_3$ | $OCH_3$ | $C_2H_5$ | $C_2H_5$ | $C_{21}H_{31}ClN_6O_6S$ |
| 13. | $OCH_2CH_2Cl$ | H | $CH_3$ | $OCH_3$ | $C_2H_5$ | $CH_2CH_2OH$ | $C_{20}H_{31}ClN_6O_7S$ |

| | | Elemental analyses | | M.p. | $CO$ $cm^{-1}$ | | nm | | Hydrolysis 20° C. |
|---|---|---|---|---|---|---|---|---|---|
| | | calcul. % | found % | °C. | mol. | ion | mol. | ion | 0.5 days |
| 1. | C | 43.0 | 42.7 42.9 | 154–6 | 1722 | 1658 | 219 | 231 | 3416 |
| | H | 5.2 | 5.3 5.5 | | | | | | |
| | N | 18.8 | 18.2 18.7 | | | | | | |
| 2. | C | 45.6 | 45.7 45.6 | 142–6 | 1730 | 1651 | 220 | 234 | 3530 |
| | H | 5.7 | 5.5 5.6 | | | | | | |
| | N | 17.7 | 17.9 18.0 | | | | | | |
| 3. | C | 44.1 | 43.9 43.0 | 142–4 | 1725 | 1655 | 221 | 233 | 3249 |
| | H | 5.5 | 5.3 5.4 | | | | | | |
| | N | 17.1 | 17.2 17.1 | | | | | | |
| 4. | C | 46.7 | 46.5 46.6 | 124–8 | 1723 | 1652 | 220 | 235 | 979 |
| | H | 5.9 | 5.8 5.9 | | | | | | |
| | N | 17.2 | 17.0 16.9 | | | | | | |
| 5. | C | 45.2 | 45.4 45.3 | 116–9 | 1721 | 1648 | 223 | 233 | 895 |
| | H | 5.8 | 5.8 5.9 | | | | | | |
| | N | 16.7 | 16.5 16.8 | | | | | | |
| 6. | C | 46.3 | 46.5 46.4 | 125–7 | 1720 | 1650 | 225 | 240 | 738 |
| | H | 6.1 | 6.1 6.0 | | | | | | |
| | N | 20.6 | 20.7 20.6 | | | | | | |
| 7. | C | 46.0 | 45.8 46.1 | 141–4 | 1718 | 1648 | 222 | 235 | 2174 |
| | H | 5.5 | 5.6 5.5 | | | | | | |
| | N | 17.9 | 17.8 17.7 | | | | | | |
| 8. | C | 48.2 | 48.3 48.4 | 123–5 | 1716 | 1642 | 224 | 233 | 2196 |
| | H | 6.0 | 6.1 5.9 | | | | | | |
| | N | 19.9 | 16.7 16.6 | | | | | | |
| 9. | C | 46.7 | 46.8 46.7 | 107–9 | 1721 | 1650 | 222 | 237 | 1837 |
| | H | 5.8 | 5.7 5.7 | | | | | | |
| | N | 16.3 | 16.2 16.2 | | | | | | |
| 10. | C | 49.2 | 49.1 49.3 | 121–4 | 1713 | 1645 | 225 | 241 | 884 |
| | H | 6.3 | 6.2 6.1 | | | | | | |
| | N | 16.4 | 16.4 16.2 | | | | | | |
| 11. | C | 47.7 | 47.9 47.8 | 112–6 | 1721 | 1652 | 221 | 234 | 796 |
| | H | 6.1 | 6.0 5.9 | | | | | | |
| | N | 15.9 | 16.1 16.2 | | | | | | |
| 12. | C | 46.3 | 46.5 46.4 | 154–8 | 1726 | 1655 | 224 | 238 | 3845 |
| | H | 6.0 | 6.1 5.9 | | | | | | |
| | N | 16.2 | 16.0 16.3 | | | | | | |
| 13. | C | 44.9 | 45.1 45.0 | 144–8 | 1718 | 1642 | 221 | 234 | 3718 |
| | H | 5.8 | 5.9 5.8 | | | | | | |
| | N | 15.7 | 15.5 15.8 | | | | | | |

TABLE 3

| | $R_7$ | $R_8$ | $R_9$ | Summary formula | Elemental analyses | | |
|---|---|---|---|---|---|---|---|
| | | | | | | % calc. | % found |
| 1. | $C_2H_5$ | $C_2H_5$ | $CH_2CH_2OH$ | $C_{14}H_{21}Cl_2NO_4$ | C | 49.7 | 49.7 49.8 |
| | | | | | H | 6.2 | 6.3 6.1 |
| | | | | | N | 4.1 | 4.0 4.2 |
| | | | | | Cl | 21.0 | 21.3 21.2 |
| 2. | $C_2H_5$ | $CH_2CH_2OH$ | $CH_2CH_2OH$ | $C_{14}H_{21}ClNO_5$ | C | 47.4 | 47.3 47.4 |
| | | | | | H | 5.9 | 5.9 6.0 |
| | | | | | N | 3.9 | 3.7 3.8 |
| | | | | | Cl | 20.0 | 19.9 19.8 |

TABLE 4

Herbicidal action of composition 1.1
Plant mass in % of controls (+ denotes increase over controls)

| IIIA | 0 | 2 | 4 | 6 | 8 | 10 |
|---|---|---|---|---|---|---|
| Wheat | | | | | | |
| 0 | | 0 | 0 | 0 | 0 | 0 |
| 10 | 0 | 0 | 0 | 0 | 0 | 0 |
| 20 | 0 | 0 | 0 | 0 | 0 | 0 |
| 30 | 0 | 0 | 0 | 0 | 0 | 0 |
| 40 | 0 | 0 | 0 | 0 | 0 | 0 |
| 50 | 0 | 0 | 0 | 0 | 0 | 0 |
| Corn | | | | | | |
| 0 | | 35 | 50 | 60 | 70 | 75 |
| 10 | 0 | 40 | 65 | 70 | 70 | 80 |
| 20 | 0 | 45 | 65 | 75 | 80 | 90 |
| 30 | 0 | 45 | 75 | 85 | 80 | 95 |
| 40 | 0 | 50 | 80 | 85 | 90 | 95 |
| 50 | 0 | 55 | 80 | 90 | 95 | 100 |
| Corn grass | | | | | | |
| 0 | | 10 | 30 | 40 | 50 | 50 |
| 10 | 0 | 40 | 40 | 60 | 60 | 70 |
| 20 | 0 | 50 | 45 | 60 | 65 | 70 |
| 30 | 0 | 45 | 50 | 65 | 65 | 75 |
| 40 | 0 | 50 | 60 | 65 | 70 | 80 |
| 50 | 0 | 50 | 60 | 70 | 70 | 85 |
| Lambsquarters | | | | | | |
| 0 | | 25 | 50 | 60 | 70 | 75 |
| 10 | 0 | 45 | 50 | 65 | 70 | 75 |
| 20 | 30 | 55 | 55 | 75 | 75 | 80 |
| 30 | 45 | 55 | 60 | 75 | 80 | 90 |
| 40 | 55 | 60 | 70 | 80 | 80 | 95 |
| 50 | 60 | 70 | 75 | 85 | 90 | 95 |
| Italian ryegrass | | | | | | |
| 0 | | 20 | 40 | 50 | 60 | 70 |
| 10 | 0 | 40 | 50 | 60 | 70 | 90 |
| 20 | 0 | 50 | 50 | 60 | 70 | 90 |
| 30 | 0 | 30 | 45 | 60 | 75 | 95 |
| 40 | 0 | 35 | 50 | 65 | 75 | 95 |
| 50 | 0 | 40 | 60 | 70 | 80 | 95 |
| Sorell | | | | | | |
| 0 | | 60 | 80 | 80 | 90 | 100 |
| 10 | 0 | 70 | 80 | 90 | 90 | 100 |
| 20 | 0 | 70 | 80 | 90 | 90 | 100 |
| 30 | 0 | 75 | 85 | 95 | 100 | 100 |
| 40 | 20 | 75 | 90 | 95 | 100 | 100 |
| 50 | 60 | 80 | 100 | 100 | 100 | 100 |
| Pigweed | | | | | | |
| 0 | | 30 | 40 | 55 | 75 | 90 |
| 10 | 0 | 40 | 50 | 60 | 80 | 90 |
| 20 | 0 | 65 | 70 | 65 | 80 | 90 |
| 30 | 20 | 65 | 75 | 80 | 85 | 100 |
| 40 | 30 | 70 | 80 | 90 | 90 | 100 |
| 50 | 40 | 70 | 80 | 90 | 95 | 100 |
| Corn poppy | | | | | | |
| 0 | | 0 | 70 | 100 | 100 | 100 |
| 10 | 0 | 30 | 90 | 100 | 100 | 100 |
| 20 | 0 | 55 | 90 | 100 | 100 | 100 |
| 30 | 20 | 60 | 90 | 100 | 100 | 100 |
| 40 | 30 | 75 | 100 | 100 | 100 | 100 |
| 50 | 50 | 100 | 100 | 100 | 100 | 100 |

TABLE 5

Herbicidal action of composition 1.2
Plant mass in % of controls (+ denotes increase over controls)

| IIIB | 0 | 2.5 | 5 | 10 | 25 | 50 |
|---|---|---|---|---|---|---|
| Wheat | | | | | | |
| 0 | | +15 | +20 | +10 | +10 | +5 |
| 5 | 0 | +10 | +10 | +5 | +5 | +10 |
| 10 | 0 | +10 | +15 | 0 | 0 | +5 |
| 15 | 0 | 0 | +10 | +10 | 0 | 0 |
| 20 | 0 | 0 | 0 | 0 | 0 | 0 |
| 25 | 0 | 0 | 0 | 0 | 0 | 0 |
| Corn | | | | | | |
| 0 | 0 | +10 | +15 | +10 | +10 | +20 |
| 5 | 0 | +10 | +10 | +10 | +20 | +20 |
| 10 | 0 | +10 | +5 | +10 | +10 | +10 |
| 15 | 0 | 0 | 0 | +5 | +5 | 0 |
| 20 | 0 | 0 | 0 | 0 | 0 | 0 |
| 25 | 0 | 0 | 0 | 0 | 0 | 0 |
| Corn grass | | | | | | |
| 0 | | 0 | 0 | 0 | 0 | 30 |
| 5 | 0 | 0 | 0 | 0 | 10 | 40 |
| 10 | 0 | 0 | 0 | 0 | 15 | 40 |
| 15 | 0 | 0 | 0 | 10 | 15 | 30 |
| 20 | 0 | 0 | 0 | 10 | 20 | 35 |
| 25 | 0 | 0 | 0 | 10 | 20 | 40 |
| Lambsquarters | | | | | | |
| 0 | | 30 | 50 | 80 | 90 | 90 |
| 5 | 0 | 40 | 65 | 85 | 95 | 95 |
| 10 | 30 | 70 | 75 | 90 | 95 | 100 |
| 15 | 45 | 75 | 80 | 90 | 100 | 100 |
| 20 | 55 | 75 | 80 | 90 | 100 | 100 |
| 25 | 60 | 80 | 90 | 95 | 100 | 100 |
| Italian ryegrass | | | | | | |
| 0 | | 0 | 10 | 20 | 25 | 40 |
| 5 | 0 | 0 | 20 | 20 | 30 | 40 |
| 10 | 0 | 30 | 35 | 40 | 45 | 65 |
| 15 | 0 | 35 | 40 | 40 | 50 | 70 |
| 20 | 0 | 40 | 45 | 40 | 50 | 70 |
| 25 | 0 | 40 | 45 | 40 | 60 | 70 |
| Sorell | | | | | | |
| 0 | | 0 | 0 | 20 | 40 | 50 |
| 5 | 0 | 0 | 10 | 30 | 45 | 60 |
| 10 | 0 | 15 | 30 | 45 | 65 | 80 |
| 15 | 0 | 20 | 40 | 65 | 70 | 80 |
| 20 | 20 | 25 | 40 | 70 | 70 | 85 |
| 25 | 60 | 35 | 50 | 70 | 80 | 80 |
| Pigweed | | | | | | |
| 0 | | 20 | 30 | 45 | 55 | 65 |
| 5 | 0 | 25 | 40 | 60 | 80 | 80 |
| 10 | 0 | 30 | 40 | 65 | 80 | 85 |
| 15 | 20 | 40 | 50 | 65 | 70 | 85 |
| 20 | 30 | 45 | 55 | 70 | 70 | 85 |
| 25 | 40 | 50 | 60 | 70 | 80 | 90 |
| Corn poppy | | | | | | |
| 0 | | 0 | 20 | 30 | 45 | 60 |
| 5 | 0 | 0 | 45 | 55 | 75 | 100 |
| 10 | 0 | 0 | 50 | 60 | 80 | 100 |
| 15 | 20 | 30 | 60 | 70 | 80 | 100 |
| 20 | 30 | 40 | 65 | 70 | 85 | 100 |
| 25 | 50 | 45 | 70 | 80 | 85 | 100 |

TABLE 6

Herbicidal action of composition 1.3
Plant mass in % of controls (+ denotes increase over controls)

| | 0 | 3 | 6 | 9 | 15 | 21 |
|---|---|---|---|---|---|---|
| Wheat | | | | | | |
| 0 | | +5 | +10 | +10 | +10 | +5 |
| 10 | 0 | +10 | +15 | +20 | +10 | 0 |
| 20 | 0 | 0 | +10 | +15 | +10 | 0 |
| 30 | 0 | 0 | 0 | +15 | +15 | 0 |
| 40 | 0 | 0 | 0 | 0 | 0 | 0 |
| 50 | 0 | 0 | 0 | 0 | 0 | 0 |
| Corn | | | | | | |
| 0 | | +5 | +10 | +20 | +10 | 0 |
| 10 | 0 | +5 | +10 | +20 | +20 | +10 |
| 20 | 0 | +10 | +15 | +20 | +10 | +10 |
| 30 | 0 | +5 | +10 | +20 | +10 | 0 |
| 40 | 0 | 0 | 0 | +10 | 0 | 0 |
| 50 | 0 | 0 | 0 | 0 | 0 | 0 |
| Corn grass | | | | | | |
| 0 | | 15 | 25 | 50 | 70 | 70 |
| 10 | 0 | 50 | 60 | 60 | 80 | 80 |
| 20 | 0 | 50 | 65 | 70 | 80 | 80 |
| 30 | 0 | 55 | 60 | 70 | 90 | 85 |
| 40 | 0 | 60 | 70 | 70 | 90 | 85 |
| 50 | 0 | 60 | 70 | 75 | 90 | 90 |
| Lambsquarters | | | | | | |
| 0 | | 30 | 55 | 70 | 80 | 90 |
| 10 | 0 | 40 | 60 | 85 | 100 | 100 |
| 20 | 30 | 50 | 60 | 90 | 100 | 100 |
| 30 | 45 | 65 | 70 | 90 | 100 | 100 |
| 40 | 55 | 70 | 75 | 90 | 100 | 100 |
| 50 | 60 | 80 | 80 | 95 | 100 | 100 |
| Italian ryegrass | | | | | | |
| 0 | | 30 | 50 | 65 | 75 | 80 |
| 10 | 0 | 50 | 65 | 80 | 85 | 100 |
| 20 | 0 | 55 | 70 | 85 | 85 | 100 |
| 30 | 0 | 60 | 70 | 85 | 90 | 100 |
| 40 | 0 | 60 | 80 | 90 | 90 | 100 |
| 50 | 0 | 65 | 70 | 90 | 90 | 100 |
| Sorell | | | | | | |
| 0 | | 50 | 80 | 90 | 95 | 100 |
| 10 | 0 | 75 | 90 | 100 | 100 | 100 |
| 20 | 0 | 80 | 90 | 100 | 100 | 100 |
| 30 | 0 | 80 | 90 | 100 | 100 | 100 |
| 40 | 20 | 90 | 95 | 100 | 100 | 100 |
| 50 | 60 | 95 | 100 | 100 | 100 | 100 |
| Pigweed | | | | | | |
| 0 | | 40 | 50 | 55 | 80 | 90 |
| 10 | 0 | 50 | 55 | 50 | 80 | 100 |
| 20 | 0 | 65 | 60 | 70 | 80 | 100 |
| 30 | 20 | 70 | 75 | 80 | 90 | 100 |
| 40 | 30 | 70 | 80 | 80 | 90 | 100 |
| 50 | 40 | 75 | 85 | 90 | 100 | 100 |
| Corn poppy | | | | | | |
| 0 | | 20 | 70 | 100 | 100 | 100 |
| 10 | 0 | 40 | 90 | 100 | 100 | 100 |
| 20 | 0 | 50 | 90 | 100 | 100 | 100 |
| 30 | 20 | 70 | 100 | 100 | 100 | 100 |
| 40 | 30 | 70 | 100 | 100 | 100 | 100 |
| 50 | 50 | 80 | 100 | 100 | 100 | 100 |

TABLE 7

Herbicidal action and synergy of composition 1.1 and mixture of sulfonylureas (MX) with Dicamba

| Composition | Dosage g/ha of act. pr. | Decrease in mass of plants [%] | | |
|---|---|---|---|---|
| | | Corn grass E | Sorrell E | Corn poppy E |
| IA | 2.0 | 10 | 60 | 0 |
| II | 32.0 | 0 | 0 | 0 |
| I.Ic | 32.0 | 45/+35 | 75/+15 | 60/+40 |
| | | *)45/+35 | 70/+10 | 60/+40 |
| | | **)43/+33 | 70/+10 | 58/+38 |
| MX(R$_1$ = Cl) + Dicamba (1:15) | 32.0 | 40/+30 | 60/0 | 50/+30 |
| | | *)25/+15 | 40/−20 | 25/+5 |
| | | **)18/+8 | 32/−28 | 20/0 |
| ID | 4.0 | 15 | 50 | 10 |
| II | 30.0 | 0 | 0 | 20 |
| I.5a | 32.0 | 50/+35 | 60/+10 | 65/+37 |
| | | *)55/+40 | 55/+5 | 65/+37 |
| | | **)48/+33 | 55/+5 | 60/+32 |
| MX(R$_1$ = OCH$_2$CH$_2$Cl) + Dicamba (1:15) | 32.0 | 40/+25 | 50/0 | 45/+17 |
| | | *)20/+5 | 15/−35 | 30/−8 |

*)The solution was kept 30 days prior to treatment
**)The solution was kept 60 days prior to treatment

TABLE 8

Effects of the herbicidal compositions based on (IA) and (II) on weeds and crop yields of spring wheat

| Example | Dosage g/ha | Weeds decr. in % | E % | Crop yield cnt/ha | Increase in yield cnt/ha |
|---|---|---|---|---|---|
| 1.1e | 25 | 60 | −13 | 21.8 | −0.7 |
| 1.1e | 50 | 90 | −7 | 22.9 | 0.4 |
| 1.1b | 25 | 50 | +4 | 22.8 | 0.3 |
| 1.1b | 50 | 90 | +8 | 26.1 | 3.6 |
| 1.1c | 25 | 50 | +22 | 26.7 | 4.2 |
| 1.1c | 50 | 95 | +31 | 30.0 | 7.5 |
| 1.1a | 25 | 40 | +10 | 23.7 | 1.2 |
| 1.1a | 50 | 80 | +16 | 25.5 | 3.0 |
| controls |  |  |  |  |  |
| (IA) | 10 | 95 |  | 25.4 | 2.9 |
|  | 5 | 70 |  | 23.1 | 0.6 |
|  | 2.5 | 40 |  | 23.5 | 1.0 |
| (II) | 150 | 70 |  | 25.6 | 3.1 |
|  | 50 | 40 |  | 22.5 | 0 |
|  | 25 | 10 |  | 21.7 | −0.8 |
| manual weeding | — | 100 |  | 25.3 | 2.3 |
|  | — | 0 |  | 22.5 | — |

$MMD_{0.5}=3.2$ cnt/ha
E—biological effect of the mixture:
(−)—antagonism
(+)—synergism
Calculated in % according to Colby equation:

$E = E_o - E_c$ wherein $E_o$—observed % of weeds destroyed by mixture
$E_c$—calculated % of weeds destroyed by mixture $E_o = X + Y - X \cdot Y / 100$ X—% of weeds destroyed by herbicide (IA)
Y—% of weeds destroyed by herbicide (II)

TABLE 9

Effects of the herbicidal compositions based on (I) and (II) on weeds and crop yields of spring wheat

| Example | Dosage g/ha | Weeds decr. % | E % | Crop yield cnt/ha | Increase in yield cnt/ha |
|---|---|---|---|---|---|
| 1.1c | 50 | 85/95 | +27/+13 | 30.0 | 7.5 |
| 1.4a | 50 | 90/100 | +25/+15 | 28.7 | 6.2 |
| 1.5a | 50 | 80/80 | +29/+10 | 25.2 | 2.7 |
| 1.6a | 50 | 60/80 | +9/+1 | 25.6 | 3.1 |
| IA | 2.5 | 40/70 |  | 23.5 | 1.0 |
| IC | 2.5 | 50/70 |  | 23.9 | 1.4 |
| ID | 2.5 | 30/65 |  | 22.7 | 0.2 |
| IF | 2.5 | 30/50 |  | 24.1 | 1.6 |
| II | 50 | 30/40 |  | 22.5 | 0 |
| manual weeding |  | 100/100 |  | 25.3 | 2.8 |
|  |  | 0 |  | 22.5 | — |

$MMD_{0.5}=3.1$ cnt/ha changes in weediness given as: number of weeds on m²/weed mass g/m²

TABLE 10

Effects of the herbicidal compositions based on (IB) and (II) on weeds and crop yields of corn

| Example | Dosage g/ha | Weeds, decrease in % of mass — millet | pigweed | Crop. yield cnt/ha | Increase in yield cnt/ha |
|---|---|---|---|---|---|
| 1.2b | 60 | 30 | 60 | 217 | 20 |
| 1.2b | 80 | 40 | 70 | 234 | 37 |
| 1.2b | 120 | 40 | 75 | 223 | 26 |
| 1.2c | 60 | 45 | 90 | 198 | 1 |
| 1.2c | 80 | 65 | 95 | 245 | 48 |
| 1.2c | 120 | 70 | 95 | 238 | 41 |
| 1.2d | 60 | 50 | 70 | 226 | 39 |
| 1.2d | 80 | 60 | 90 | 234 | 37 |
| 1.2d | 120 | 75 | 90 | 218 | 21 |
| controls |  |  |  |  |  |
| IB | 50 | 15 | 60 | 231 | 34 |
| II | 150 | 30 | 70 | 221 | 24 |
| no herbicide | — | 0 | 0 | 197 | — |

$MMD_{0.5}=30$ cnt/ha

Formulas for tables 8, 9, 10

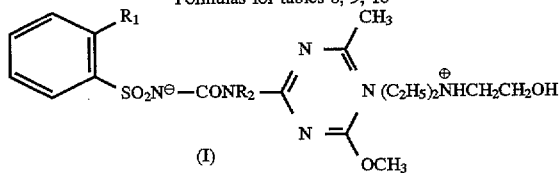

(I)

IA: $R_1 = Cl$    $R_2 = H$
IC: $R_1 = CO_2CH_3$    $R_2 = H$
ID: $R_1 = OCH_2CH_2Cl$    $R_2 = H$
IF: $R_1 = CO_2CH_3$    $R_2 = CH_3$

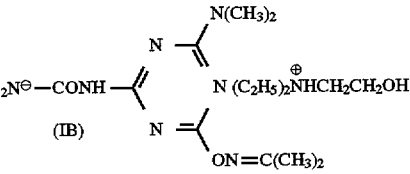

(IB)

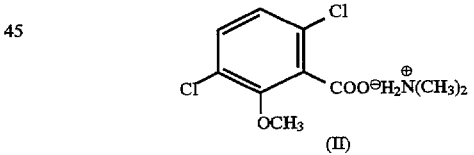

(II)

I claim:

1. A herbicidal composition for use in cereals, comprising at least one benzenesulfonylurea derivative and at least one dichlorobenzoic acid derivative in synergistic herbicidally effective amounts, a surfactant, an organic solvent, and water, wherein the benzenesulfonylurea derivative is of the formula (I)

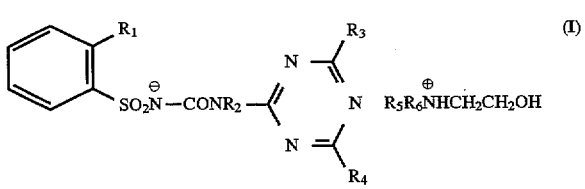

(I)

wherein:

$R_1$ is Cl;

$R_2$ is H;

$R_3$ is $CH_3$;

$R_4$ is $OCH_3$;

$R_5$ is $C_2H_5$; and $R_6$ is $C_2H_5$;

and the derivative of dichlorobenzoic acid is a 2-methoxy-3,6-dichlorobenzoic acid of the formula (II)

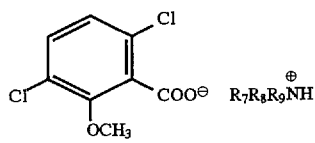

wherein:

$R_7$ is $CH_3$;

$R_8$ is $CH_3$; and $R_9$ is H;

with the following weight percentages of compounds:

| | |
|---|---|
| ammonium salt of benzenesulfonylurea derivative | 2.0–50 |
| ammonium salt of 2-methoxy-3,6-dichlorobenzoic acid | 5.0–50 |
| surfactant | 1.0–5.0 |
| organic solvent | 10–40 |
| water | up to 100. |

2. The herbicidal composition of claim 1, wherein the surfactant is selected from the group consisting of bis-polyoxyethylated alkylamine, sodium bis(2-ethylhexyl) succinate sulfonate, polyethyleneglycol monoalkyl ethers, and alkylaryl ethers of polyethyleneglycol or polypropyleneglycol.

3. The herbicidal composition of claim 1, wherein the organic solvent is triethyleneglycol.

4. A herbicidal composition for use in cereals, comprising synergistic herbicidally effective amounts of:

2.0 weight percent of a benzenesulfonylurea derivative of formula (I)

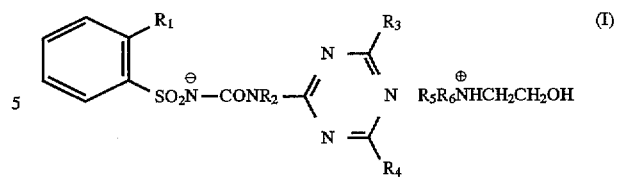

wherein:

$R_1$ is Cl;

$R_2$ is H;

$R_3$ is $CH_3$;

$R_4$ is $OCH_3$;

$R_5$ is $C_2H_5$; and $R_6$ is $C_2H_5$;

40 weight percent of an ammonium salt of 2-methoxy-3,6-dichlorobenzoic acid of formula (II)

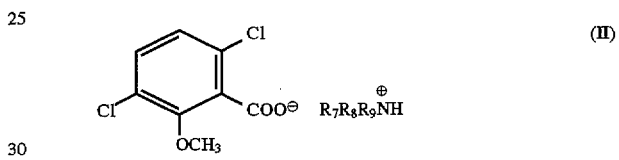

wherein:

$R_7$ is $CH_3$;

$R_8$ is $CH_3$; and $R_9$ is H;

3.0 weight percent of a surfactant selected from the group consisting of bis-polyoxyethylated alkylamine, sodium bis (2-ethylhexyl) succinate sulfonate, polyethyleneglycol monoalkyl ethers, and alkylaryl ethers of polyethyleneglycol or polypropyleneglycol;

20 weight percent of triethylene glycol; and 35 weight percent of water.

5. A method for control of undesired vegetation in cereals comprising treating an area under crops with a herbicidal composition comprising a derivative of benzenesulfonylurea and a derivative of dichlorobenzoic acid in synergistic herbicidally effective amounts, a surfactant, an organic solvent, and water, wherein the derivative of benzenesulfonylurea is of the formula (I)

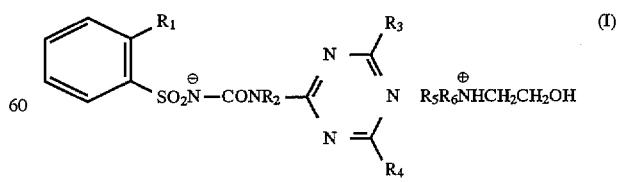

wherein:
- $R_1$ is Cl;
- $R_2$ is H;
- $R_3$ is $CH_3$;
- $R_4$ is $OCH_3$;
- $R_5$ is $C_2H_5$; and
- $R_6$ is $C_2H_5$;

and the derivative of dichlorobenzoic acid is a 2-methoxy-3,6-dichlorobenzoic acid of the formula (II)

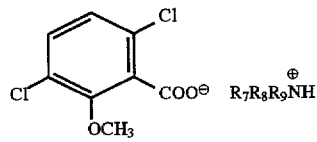 (II)

wherein:
- $R_7$ is $CH_3$;
- $R_8$ is $CH_3$; and
- $R_9$ is H;

with the following weight percentages of compounds:

| | |
|---|---|
| ammonium salt of benzenesulfonylurea derivative | 2.0–50 |
| ammonium salt of 2-methoxy-3,6-dichlorobenzoic acid | 5.0–50 |
| surfactant | 1.0–5.0 |
| organic solvent | 10–40 |
| water | up to 100. | with the application dosage of active principles being in the range of 25–125 g/ha.

* * * * *